United States Patent [19]

Wallach

[11] 4,138,205
[45] Feb. 6, 1979

[54] MOVABLE STATOR WALLS PERMITTING ACCESS TO TUBING IN PERISTALTIC PUMP

[75] Inventor: Mark Wallach, New York, N.Y.

[73] Assignee: Hydro Pulse Corporation, New York, N.Y.

[21] Appl. No.: 641,103

[22] Filed: Dec. 15, 1975

[51] Int. Cl.$^2$ .................... F04B 43/08; F04B 43/12; F04B 45/06
[52] U.S. Cl. .................................. 417/360; 417/477
[58] Field of Search ............... 417/360, 477, 476, 475; 222/214; 418/39, 70, 45

[56] References Cited

U.S. PATENT DOCUMENTS

| | | | |
|---|---|---|---|
| 487,136 | 11/1892 | Truax | 417/477 |
| 2,585,949 | 2/1952 | MacCormack | 417/476 |
| 2,679,807 | 6/1954 | Bruckmann | 417/476 |
| 3,038,414 | 6/1962 | Margus | 418/70 |
| 3,431,864 | 3/1969 | Jones | 417/477 |
| 3,674,383 | 7/1972 | Ices | 417/476 |
| 3,841,799 | 10/1974 | Spinosa et al. | 417/475 |
| 3,927,955 | 12/1975 | Spinosa et al. | 417/477 |

Primary Examiner—John J. Vrablik
Assistant Examiner—Thomas I. Ross
Attorney, Agent, or Firm—Howard C. Miskin

[57] ABSTRACT

A tubing replaceable, peristaltic pump includes a base plate and a rotor mounted on the base plate and having peripherally spaced thrust rollers. Pivotally mounted on the base plate on opposite sides of the rotor are a pair of stator members which are swingable about proximate laterally spaced ends thereof between closed and open positions with their inner concave cylindrical faces confronting the rotor being respectively proximate and coaxial with the rotor and remote from the rotor. Hand operated devices are located at the free ends of the stator members and swing the stator members between locked closed positions and open positions. A flexible collapsible tube is entrapped between the rotor and closed stator members and is replaceable when the stator members are in opened position, the tube extending radially outwardly between the stator member laterally spaced front ends. If desired the stator members are reciprocatable towards and away from the rotor.

7 Claims, 5 Drawing Figures

MOVABLE STATOR WALLS PERMITTING ACCESS TO TUBING IN PERISTALTIC PUMP

BACKGROUND OF THE INVENTION

The present invention relates generally to improvements in fluid pumps and it relates more particularly to an improved tubing or peristaltic type of pump.

The conventional positive displacement pump or metering device such as the piston pump, gear pump or the like, possess numerous drawbacks and disadvantages when employed on many procedures and with many types of fluids. It is difficult and often impossible to isolate the fluid medium from the pump ambient environment and from contamination and problems are encountered when the pumped fluid is a slurry, sterile, or of a highly corrosive or abrasive nature. The above drawbacks are overcome by the use of a tubing or peristaltic type of pump which generally includes a compressible tube to which advancing constrictions are imparted by a rotating rotor having thrust rollers which successively engage the tube and compress it against a backing stator surface. While the peristaltic pump is highly superior in many applications it is characterized by the requirement that the compressible tube be frequently replaced due to its failure by fatigue and abrasion and by changes in application. The replacement of the peristaltic tube in the pumps heretofore available and proposed is a difficult and time-consuming procedure and these pumps otherwise leave much to be desired.

SUMMARY OF THE INVENTION

It is accordingly a principal object of the present invention to provide an improved pump.

Another object of the present invention is to provide an improved closed path metering pump.

Still another object of the present invention is to provide an improved peristaltic type fluid pump.

A further object of the present invention is to provide an improved peristaltic pump in which the peristaltic tube may be rapidly and easily replaced.

Still a further object of the present invention is to provide a pump of the above nature characterized by its reliability, simplicity, ruggedness, low cost, ease of servicing and high versitility and adjustability.

The above and other objects of the present invention will become apparent from a reading of the following description taken in conjunction with the accompanying drawings which illustrate a preferred embodiment thereof.

In a sense the present invention comtemplates the provision of an improved tubing or peristaltic pump comprising a base member, a rotor having a series of peripherally spaced thrust elements disposed in the base member and rotatable about a longitudinal axis, a stator member having a concave face confronting the periphery of the rotor and mounted on the base member and being transversely movable between a closed position with the stator concave face proximate the rotor and an open position with the stator face remote from the rotor, a mechanism for releasably locking the stator member in its locked position and a resilient collapsible tube disposed between the rotor and stator faces and compressed by successive thrust elements against the stator face when the stator member is in closed position and movable from between the rotor and stator member when the stator member is in open position.

In the preferred form of the improved peristaltic pump the rotor includes a hub journalled in a bore in the base member and a pair of axially spaced discs on the hub between which the thrust members which consist of freely rotatable rollers are supported. A pair of stator members on opposite sides of the rotor is provided, the stator members being pivoted to the base member at proximate ends of the stator members, each of the stator members being provided with a hand manipulated mechanism at its free end for transferring the respective stator member between a locked closed position and an open position. The faces of the stator members, in their closed positions, are arcuate and cylindrical and coaxial with the rotor, the tube extending between the rotor and stator faces and outwardly thereof between the pivoted ends of the stator members.

The improved pump operates in the manner of the conventional peristaltic pump, but the peristaltic tube may be rapidly, reliably and easily replaced merely by the simple manipulation of the stator opening mechanism, the replacement of the peristaltic pipe and the closing of the stator. The pump is simple, rugged, reliable, of low cost and of great versitility and adaptability.

DESCRIPTION OF THE PREFERRED EMBODIMENT

Figure 1:
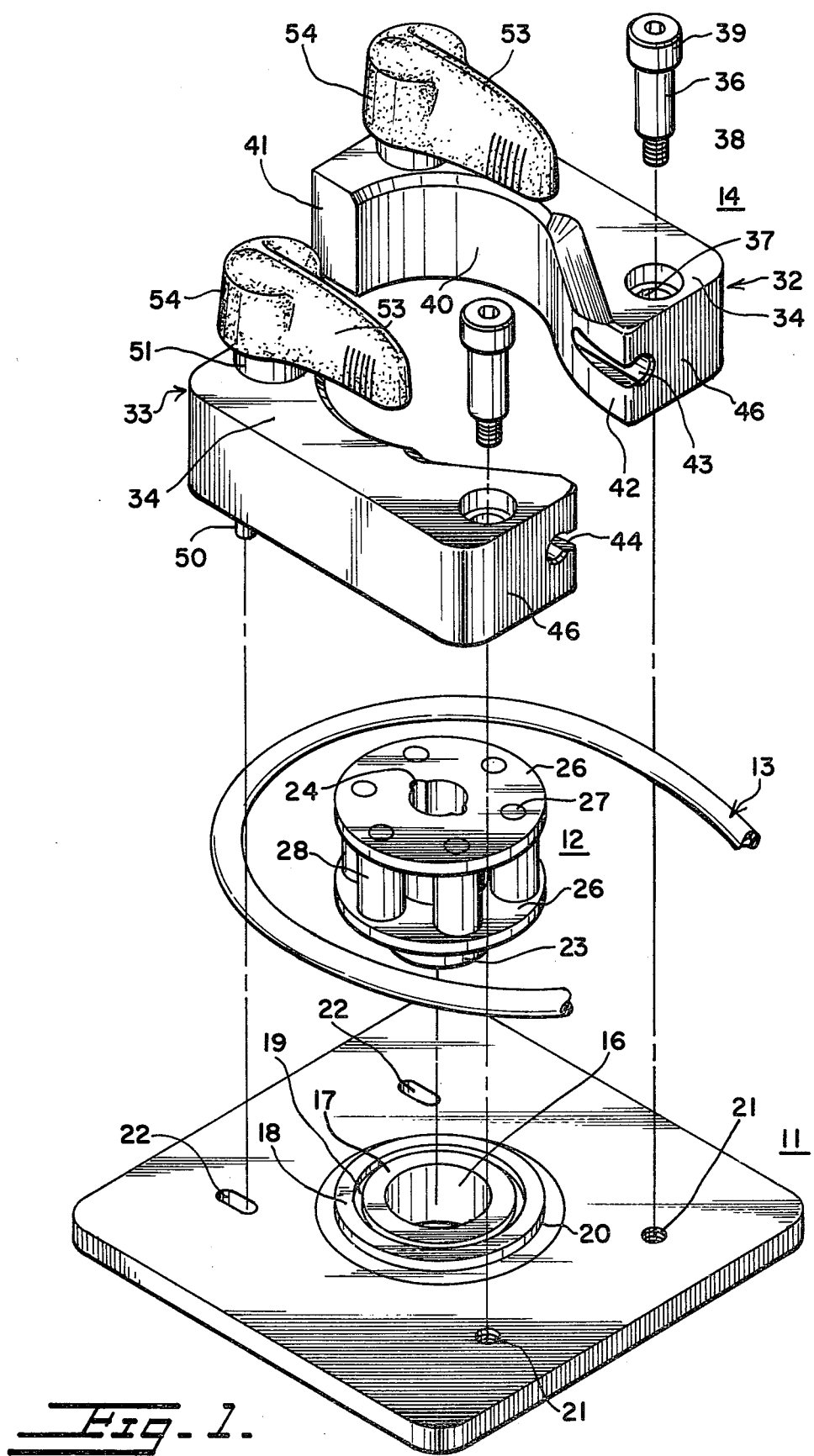
FIG. 1 is an exploded perspective view of a peristaltic pump embodying the present invention.

Referring now to the drawings which illustrate a preferred embodiment of the present invention, the reference numeral 10 generally designates an improved peristaltic pump, the various parts of which are fabricated of approximately suitable materials. The pump 10 primarily includes a mounting base member or plate 11, a rotor 12, a peristaltic tube 13 and a stator assembly 14.

The base plate 11 is suitably mounted and stationary and of square configuration and has a central bore 16 bordered by a flat topped raised annular ridge 17 which, in turn, is surrounded by a coaxial flat topped raised annular ridge 18 opened from ridge 17 by an annular channel 19 and from the top face of base plate 11 by an annular channel 20. Formed in the front border of base plate 11 is a symmetrically spaced pair of threaded openings 21 and in the rear border thereof a symmetrical pair of slightly forwardly converging short linear cam grooves 22.

The rotor 12 includes a hollow shaft or hub 23 whose lower end is journalled in base 16 and which has formed in its inner face diametrically opposed longitudinal keyways 24. A pair of axially spaced upper and lower discs 26 are secured to the hub 23 the lower disc resting on the flat top flat of ridges 17 and 18 and the upper disc being at the top of hub 23. A plurality of regularly peripherally spaced axles 27, illustrated as six in number, although nine or less may be employed, are supported by and between the borders of the discs 26, each of the axles 27 supporting a thrust element defining freely rotatable coaxial roller 28 which extends between the confronting faces of discs 26. The shaft of a preferably adjustable speed drive motor, now shown, engages the bore of, and is coupled to, the rotor 12 by way of key ways 24.

The stator assembly 14 is mounted atop the base plate 11 and comprises a pair of symmetrical similarly shaped opposite sections 32 and 33 which are laterally spaced and disposed symmetrically relative to the medial transverse axis of the base plate 11. Each stator section 32 and 33 includes a stator member block 34 which extends transversely and is pivotally connected proximate its forward end to the base plate 11 for swinging about a longitudinal axis by a pivot pin 36 engaging a vertical bore 37 in the stator member front end and having a threaded reduced diameter free end position 38 engaging a corresponding tapped bore 21 in base plate 11. The enlarged head 39 of pivot pin 36 nests in an enlarged upper counter bore of bore 37.

The inside pressure or clamp face 40 of stator blocks 34 is of concave arcuate cylindrical configuration and extends for somewhat less than 180° from a flat radial rear inside end face 41 to a slightly convex inside front end face 42. When the stator members 34 are in their closed position the end faces 41 are in coinciding abutting engagement, the pressure faces 40 form a continuous arcuate cylindrical surface of somewhat less than 360 degrees and the faces 42 are laterally spaced and delineate a radial throat between the area delineated by the cylindrical face 40 and the exterior face of the stator. Formed in each of the throat faces 42 and extending medially along the length thereof is a guide groove 43 of arcuate transverse cross section, the base of the groove 43 coverging with the respective throat face 42 at its inner end, the side opening 44 to the groove 43 being somewhat restricted proximate its outer end and the groove 43 communicating with the front face 46 of the stator member 34.

Formed in the rear portion of each stator block 34 is a vertical bore which terminates at its bottom in a shallow enlarged counterbore 47. A shaft 38 is journalled in and traverses the vertical bore and has affixed to its bottom a coaxial disc 49 which nests in the counterbore 47 and is provided with a depending pin 50 which slidably engages a corresponding cam groove 22 and is eccentric to the axis of shaft 48 and disc 49. A cap member 51 engages the upper end of shaft 48 immediately above the stator member 34 and is affixed thereto by a set screw 52 and a hand or manipulating lever 53 terminates at its inner end in a cap portion 54 which engages the top of cap member 51 and is adjustably affixed thereto by a set screw 56.

Figure 2:
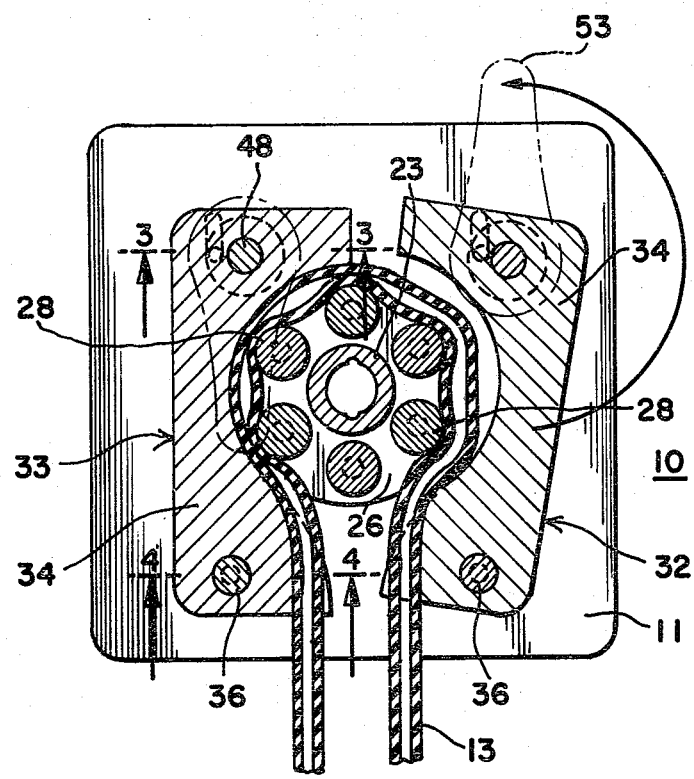
FIG. 2 is a horizontal sectional view thereof showing one of the stator members in open position.
Figure 3:
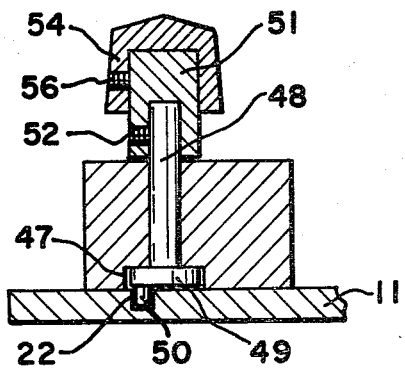
FIG. 3 is a sectional view taken along line 3—3 in FIG. 2.
Figure 4:
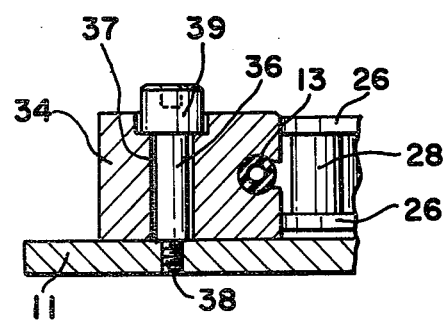
FIG. 4 is a sectional view taken along line 4—4 in FIG. 2.

The cam grooves 22, eccentric pins 50 and hand levers 53 are so angularly related that when the respective hand lever 53 is forwardly directed, the corresponding stator section, for example stator section 33 as shown in FIG. 2, is in its locked closed position proximate the rotor 12 with the eccentric pin 50 engaging the forward end of a cam groove 22 and when the hand lever 53 is rearwardly directed, as shown by stator section 32 in FIG. 2, the stator section 34 is in its open position remote from the rotor 22 with the eccentric pin 50 engaging rearward end of cam groove 22. In transferring a stator member 34 between its open and closed positions a corresponding hand lever 53 is merely rotated about 180 degrees and this orbits the shaft 48 about pins 36 and 50, the pin 50 reciprocating along a corresponding cam groove 22 and the stator member swinging between its open and closed positions.

The peristaltic tube 13 is formed of a compressible resilient material, for example a natural rubber or a synthetic plastic, such as Tygon, silicone rubber or the like. In the operative condition of the peristaltic pump 10 the stator members 34 are in their locked closed condition with the hand levers 53 forwardly directed, the end faces 41 in abutment and the stator pressure faces 40 in closed proximate positions relative to the thrust rollers 28. The peristaltic tube 13 extends along the respective passageways or grooves 43 and about the rotor 12 between the rotor 12 and the stator pressure faces 40, being entrapped between the rotor and pressure faces, the thrust rollers 28 compressing and constricting longitudinally spaced areas of the tube and advancing such constrictions with the rotation of the rotor to effect a peristaltic pumping action in the known manner.

In order to replace the peristaltic tube 13, the hand levers 53 are swung to their rearwardly directed positions to unlock and open the stator sections 32 and 33 and release the peristaltic tube 13 which is then easily removed from between the rotor and stator faces and passageways 43 and replaced by another peristaltic tube 13 which is positioned along passageways 43 and about the rotor 12, between the rotor and the open stator members. The stator sections are then closed by merely swinging the hand levers 53 to their forwardly directed lock positions and the peristaltic pump 10 is thus in an operative condition.

Figure 5:
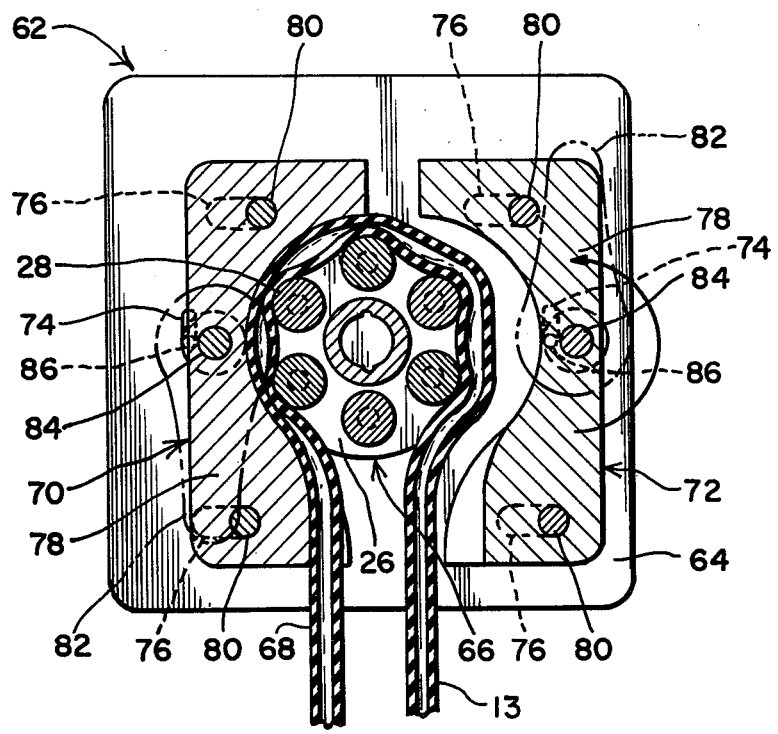
FIG. 5 is a horizontal sectional view of another embodiment similar to FIG. 2 showing one of the stator members in open position.

Another embodiment of the present invention is illustrated in FIG. 5 which shows a pump 62, similar to the embodiment described above, the includes a mounting base plate member 64, a rotor 66 and a peristaltic tube, and a pair of symmetrical, similarly shaped, opposite stator sections 70 and 72.

Base plate 64 is generally similar to base plate 11 described above, except that the symmetrically spaced pair of laterally converging, short, linear cam grooves 74 are positioned centerally on opposite sides of rotor 66. Formed on each side of rotor 66 and on opposite sides of each of cam grooves 74 are a pair of elongated parallel slots 76.

Rotor 66 is generally similar to rotor 12 described above. Stator sections 70 and 72 are laterally spaced and disposed symmetrically relative to the medial transverse axis of base plate 64. Each stator section 70 and 72 includes a stator member block 78 which extends transversely of, and reciprocates towards and away from rotor 66, by means of the pair of pins 80 extending downwardly from each of blocks 78 into corresponding elongated slots 76 in plate 64.

The inside pressure or clamp face of stator sections 70 and 72 are concave arcuate cylindrical configuration like stator members 32 and 34 of the first-described embodiment.

Formed centerally in each stator block 78 is a vertical bore and a shaft 84. A hand or manipulating lever 82 is fixedly attached to shaft 84. The cam grooves 74 receive a pin 86, which is coupled to shaft 84 in a manner similar to that described above with respect to the first embodiment. The cam grooves 74 and pins 86 and the hand levers 82 are so angularly related that when a respective hand lever 82 is rotated, it either locks stator block 78 in its locked closed position proximate the rotor 66 with the eccentric pin 86 engaging the forward end of cam groove 74, or when the hand lever 82 is rearwardly directed, as is shown in the right stator block 78, the stator block is in its open position remote from rotor 66 with the eccentric pin 74 engaging the forward end of cam groove 74. In reciprocating stator blocks 78 between open and closed position, relative to rotor 66, the corresponding hand lever 82 is merely rotated about 180 degrees. Stator blocks 78 reciprocate along elongated slotted openings 76.

The peristaltic tube 68 is similar to tube 13 described above.

The pump 62 is operated in a manner similar to that described above and the peristaltic tube 68 can be easily replaced in a manner generally similar to that described above when the stator blocks are in their open position.

When the stator blocks 34 and 78 have been described as generally symmetrical, they can be varied with each pump to provide for different operating characteristics.

Also while at high speeds the tube 68 may creep because of the action of rotor 66, molded rings can be positioned at pre-determined locations along the length of tube 68, so that the rings abut the outer edges of block 34 or 78 to provide tension of the tube around the rotor. This resists the elongation or creep.

Also, while both stator blocks were shown to be movable, if desired only a single block need be movable and the tube be angled in contact with the rotor for about 180° in circumference.

While there has been described and illustrated a preferred embodiment of the present invention, it is apparent that numerous alternations, omissions and additions may be made without departing from the spirit thereof.

I claim:

1. A peristaltic pump comprising a base member, a rotor having a plurality of peripherally spaced thrust elements disposed on said base member, said rotor being rotatable about a longitudinal axis, a pair of stator members disposed in opposite sides of said rotor, each stator member having a concave face confronting the periphery of said rotor, said stator members being pivoted, at laterally spaced apart proximate first ends thereof, to said base member for swinging about respective longitudinal axes between relative closed positions with said stator faces proximate said rotor and an open position with said stator faces remote from rotor wherein when said stator members are in their closed positions the said first ends thereof are laterally spaced and the respective opposite second ends thereof are in substantially abutting engagement, means for releaseably locking said stator members in their closed positions, and a resilient collapsible tube disposed between said rotor and said stator member faces and compressed by successive thrust elements against said stator member faces when said stator members are in closed position and removable from between said rotor and stator members when said stator members are in open position.

2. The peristaltic pump of claim 1 wherein said faces of said stators when in closed positions define a cylindrical arcuate surface coaxial with said rotor.

3. The peristaltic pump of claim 1 wherein the confronting faces of said stator members proximate the first ends thereof have passageways formed therein extending between said concave cylindrical faces and the outside end faces of said stator members, said tube extending along and nesting in said passageways.

4. The peristaltic pump of claim 1 wherein said stator member locking means are manually operable and swing said stator members between their open and closed positions.

5. The peristaltic pump of claim 1 wherein said rotor comprises a hub and a pair of axially spaced coaxial discs mounted on said hub, said thrust elements comprising freely rotatable longitudinally extending rollers supported between the binders of said discs.

6. A peristaltic pump comprising a base member, a rotor having a plurality of peripherally spaced thrust elements disposed on said base member said rotor being rotatable about a longitudinal axis, a pair of laterally spaced stator members having concave faces confronting the periphery of said rotor, said stator members being mounted on said base member and laterally reciprocatable thereon relative to said rotor between closed positions with said stator faces proximate said rotor and open positions with said stator faces remote from said rotor, said stator members in said closed positions having corresponding first ends thereof defining a transverse throat and opposite corresponding second ends in substantially abutting engagement, an actuating arm on at least one of said pair of stator members connected to means extending through said one stator member and cooperating with the base member for reciprocating said one stator member to its open and closed positions, means for releaseably locking said stator members in their closed positions and a resilient, elongated, collapsable tube extending peripherally along and disposed between said rotor and said stator faces and extending through said throat and compressed by successive thrust elements against said stator faces when said stator members are in closed position and movable from between said rotor and stator members when said stator members are in open position.

7. The peristaltic pump of claim 6 wherein said base member has laterally spaced laterally extending slots formed therein and including follower members depending from said stator members into sliding engagement with said slots.

* * * * *